United States Patent
Reyes et al.

(10) Patent No.: US 9,427,508 B2
(45) Date of Patent: Aug. 30, 2016

(54) AXIAL FLOW PUMP PRESSURE ALGORITHM

(71) Applicant: HeartWare, Inc., Miami Lakes, FL (US)

(72) Inventors: Carlos Reyes, Davie, FL (US); Fernando Casas, Miami Lakes, FL (US); Justin Wolman, Aventura, FL (US)

(73) Assignee: HeartWare, Inc., Miami Lakes, FL (US)

( * ) Notice: Subject to any disclaimer, the term of this patent is extended or adjusted under 35 U.S.C. 154(b) by 190 days.

(21) Appl. No.: 14/294,448

(22) Filed: Jun. 3, 2014

(65) Prior Publication Data

US 2014/0357937 A1    Dec. 4, 2014

Related U.S. Application Data

(60) Provisional application No. 61/831,023, filed on Jun. 4, 2013.

(51) Int. Cl.
| | |
|---|---|
| *A61B 5/04* | (2006.01) |
| *A61M 1/10* | (2006.01) |
| *A61M 1/12* | (2006.01) |

(52) U.S. Cl.
CPC ........... *A61M 1/1086* (2013.01); *A61M 1/101* (2013.01); *A61M 1/122* (2014.02)

(58) Field of Classification Search
USPC ........................................................ 600/17
See application file for complete search history.

(56) References Cited

U.S. PATENT DOCUMENTS

| | | |
|---|---|---|
| 6,527,699 B1 | 3/2003 | Goldowsky |
| 2004/0241019 A1 | 12/2004 | Goldowsky |
| 2008/0262289 A1 | 10/2008 | Goldowsky |
| 2012/0245681 A1 | 9/2012 | Casas et al. |
| 2013/0041204 A1* | 2/2013 | Heilman ................. A61M 1/10 600/17 |

OTHER PUBLICATIONS

Partial Intenational Search Report for Application No. PCT/US3014/040803 dated Sep. 25, 2014.

* cited by examiner

*Primary Examiner* — Nicole F Lavert
(74) *Attorney, Agent, or Firm* — Lerner, David, Littenberg, Krumholz & Mentlik, LLP

(57) ABSTRACT

The presence or absence of a high pressure condition in an implantable blood pump is determined at least in part based on a comparison between a determined amount of differential pressure across the pump and a pressure threshold value. The amount of differential pressure parameter may be determined based at least in part on a parameter related to flow, such as a parameter related to thrust on the rotor of the pump. In response to determining the presence of a high pressure condition, an updated speed of rotation of the rotor that is less than the rotor's initial speed may be determined. The rotor's speed may be increased when the flow rate of blood is determined to be at least equal to a flow recovery threshold value.

36 Claims, 13 Drawing Sheets

AXIAL FLOW PUMP PRESSURE ALGORITHM

CROSS-REFERENCE TO RELATED APPLICATIONS

The present application claims the benefit of the filing date of U.S. Provisional Patent Application No. 61/831,023 filed Jun. 4, 2013, the disclosure of which is hereby incorporated herein by reference.

FIELD OF THE INVENTION

The present invention relates to blood pumps, to methods of using blood pumps, and to control circuits adapted for use with blood pumps.

BACKGROUND OF THE INVENTION

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as ventricular assist device or "VAD." Where a VAD is used to assist the pumping action of the left ventricle, the device draws blood from the left ventricle of the heart and discharges the blood into the aorta.

To provide clinically useful assistance to the heart, blood pumps impel blood at a substantial blood flow rate. For an adult human patient, a ventricular assist device may be arranged to pump blood at about 1-10 liters per minute at a differential pressure across the pump of about 10-110 mm Hg, depending on the needs of the patient. The needs of the patient may vary with age, height, and other factors.

During operation, the differential pressure across the pump may increase. This increase of differential pressure may be harmful to the patient, and may be indicative of either a suction condition or occlusion within the pump. Therefore, it would be desirable to provide a blood pump controller which can monitor the differential pressure across the pump and can control operation of the pump in order to avoid harmful pressure buildups.

Operation of some blood pumps may be controlled in response to a determined flow rate at the pump. For example, pending U.S. Publication No. 2012/0245681, the disclosure of which is hereby incorporated herein in its entirety, describes a method of operating a blood pump using a control circuit that detects a low flow condition, characterized by a low flow rate, and commands a drive circuit of the pump to cause a momentary reduction in the pump speed in order to cure the low flow condition. Although clearance of the low flow condition may have the further benefit of reducing differential pressure across the blood pump, it is possible to encounter a pressure buildup across the pump before a low flow condition is detected. Therefore, it would be further desirable to be able to prevent pressure build up in the blood pump without having to detect a low flow condition.

BRIEF SUMMARY OF THE INVENTION

One aspect of the present disclosure is directed to an implantable blood pump system. The system may include a pump, including a housing having an axis, and a rotor disposed within the housing. The rotor may be rotatable around the axis. The system may further include a control circuit operatively coupled to the pump and configured to determine a flow rate of blood based at least in part on a parameter related to thrust on the rotor along the axis, and to determine a pressure condition of the pump based at least in part on the flow rate of blood. The pressure condition may be a condition under which differential pressure across the pump equals or exceeds a threshold pressure value.

In one example, the pump may include a stator operatively coupled to the control circuit and incorporating a plurality of coils for applying a rotating magnetic field to the rotor. In such an example, the parameter may be based on back electromotive force (BEMF) in one or more of the plurality of coils. In some examples, the control circuit may include a processor coupled to a memory, the memory storing a table that relates flow rates to corresponding amounts of differential pressure at the blood pump. The control circuit may also, or alternatively, be operative to determine the differential pressure based on the flow rate and speed of rotation of the rotor.

Another aspect of the disclosure is directed to a control circuit for monitoring the operation of an implantable blood pump. The control circuit may include a flow rate determination circuit operative to determine a flow rate of blood based at least in part on a parameter related to thrust generated by a rotor of the pump, a pump pressure condition determination circuit operative to determine a pressure condition of the pump based at least in part on the determined flow rate of blood. The pressure condition as explained above, may be a condition under which differential pressure across the pump equals or exceeds a threshold pressure value.

In some examples, the control circuit may further be operable to sample voltage across a first coil of a stator of the pump during an open-phase period in which: (i) the first coil is not being driven, and (ii) at least one other coil in the stator is being driven; so as to evaluate a function of back electromotive force (BEMF) during the open-phase period. The flow rate may then be determined based at least in part on the function of BEMF and speed of rotation of the rotor. In some such examples, the function of BEMF may be a rate of change of the BEMF.

The control circuit may further include a processor and memory coupled to the processor, and, as above, the memory may store a table that relates different flow rates to different amounts of differential pressure at the blood pump for a given speed of rotation of the rotor. The control circuit may further, or alternatively, include a pump control module operative to control operation of the pump based at least in part on the determined pressure condition.

A further aspect of the disclosure is directed to a method for monitoring operation of an implantable blood pump, including determining a flow rate of blood through the pump based at least in part on (i) a parameter relating to thrust generated by a rotor of the pump and (ii) speed of rotation of a rotor of the pump, and determining a pressure condition of the pump based at least in part on the flow rate of blood. In some examples, the flow rate of blood through the pump may further be based on the magnitude of a current supplied to the pump. Some examples also provide for controlling the operation of the pump based on the determined pressure condition.

Yet another aspect of the disclosure provides for an implantable blood pump system including a pump, rotor and control circuit operatively coupled to the pump and configured to: determine a differential pressure across the blood pump based at least in part on an initial speed of rotation of the rotor; compare the differential pressure to a threshold pressure value; determine the presence or absence of a high pressure condition based at least in part on the comparison; and in response to determining the presence of a high pressure condition, determine an updated speed of rotation of the rotor, the updated speed being less than the initial speed. In one example, the control circuit may further be operative to determine differential pressure based further on a flow rate of blood. In another example, the control circuit may further include a pump control module operative to control operation of the pump based on the updated determined speed. In a further example, the control circuit may include a processor coupled to a memory, the memory storing one or more tables, the one or more tables relating flow rates to corresponding differential pressure values for a given speed of rotation of the rotor, wherein at least one table relates flow rates to differential pressure values at the initial speed. In yet another example, the control circuit may be operative to determine the updated speed based on the speed of the rotor at which the presence of a high pressure condition is determined.

In some examples, the control circuit may also determine differential pressure across the blood pump at the updated speed, and may further be operative to delay such determination for a predetermined amount of time based on a count value indicative of a number of recovery attempts initiated.

Yet a further aspect of the disclosure provides for a control circuit for monitoring the operation of an implantable blood pump. The control circuit may include a differential pressure determination circuit, a pressure condition determination circuit, and an operating speed determination circuit, the operating speed determination circuit operative to determine a reduced speed of rotation of the rotor based on the determination of the pressure condition determination circuit. In some examples, the control circuit may further include a flow rate determination circuit operative to determine a flow rate of blood, and a flow recovery determination circuit operative to determine whether the determined flow rate of blood is at least equal to a flow recovery threshold value. In such examples, the operating speed determination circuit may be further operative to determine an increased speed of rotation of the rotor if the determined flow rate of blood is at least equal to a flow recovery threshold value. Additionally or alternatively, the flow recovery threshold value may be based on the speed of the rotor during determination of the flow rate of blood.

An even further aspect of the present disclosure provides for a method of monitoring operation of an implantable blood pump, including: determining an amount of differential pressure across the pump at an initial speed of rotation of a rotor of the pump; comparing the amount of differential pressure to a differential threshold pressure value; determining the presence or absence of a high pressure condition at least partially based on the comparison; and in response to determining the presence of a high pressure condition, determining an updated speed of rotation of the rotor less than the initial speed. The method may further involve determining a flow rate of blood and whether the determined flow rate of blood is at least equal to a flow recovery threshold value. If the determined flow rate of blood is at least equal to a flow recovery threshold value, the method may further involve increasing the speed of rotation of the rotor. The flow recovery threshold value may be based on the speed of the rotor during the determination of the flow rate of blood, and the updated speed of rotation of the rotor may be determined based on a count value indicative of a number of recovery attempts initiated.

In some examples, the method may be repeatedly performed to regulate differential pressure across the pump. In some such examples, performance of the method may be delayed for a predetermined amount of time based on the determination of the presence of a high pressure condition and a count value indicative of a number of recovery attempts initiated. Additionally, or alternatively, performance of the method may be ceased based on the determination of the presence of a high pressure condition and a count value indicative of a number of retry cycles initiated.

There are various devices, systems and methods for providing effective, long term and reliable use of pressure feedback in VADs. Exemplary embodiments are described which provide for direct left ventricle pressure measurement, non-invasive calibration techniques to detect ventricular collapse and recalibrate the feedback mechanism, improved pressure sensor designs with reduced drift, and barometric pressure correction schemes. These devices and methods may be used alone or in combination with each other, and may also be combined with other feedback mechanisms.

DETAILED DESCRIPTION

Figure 1:
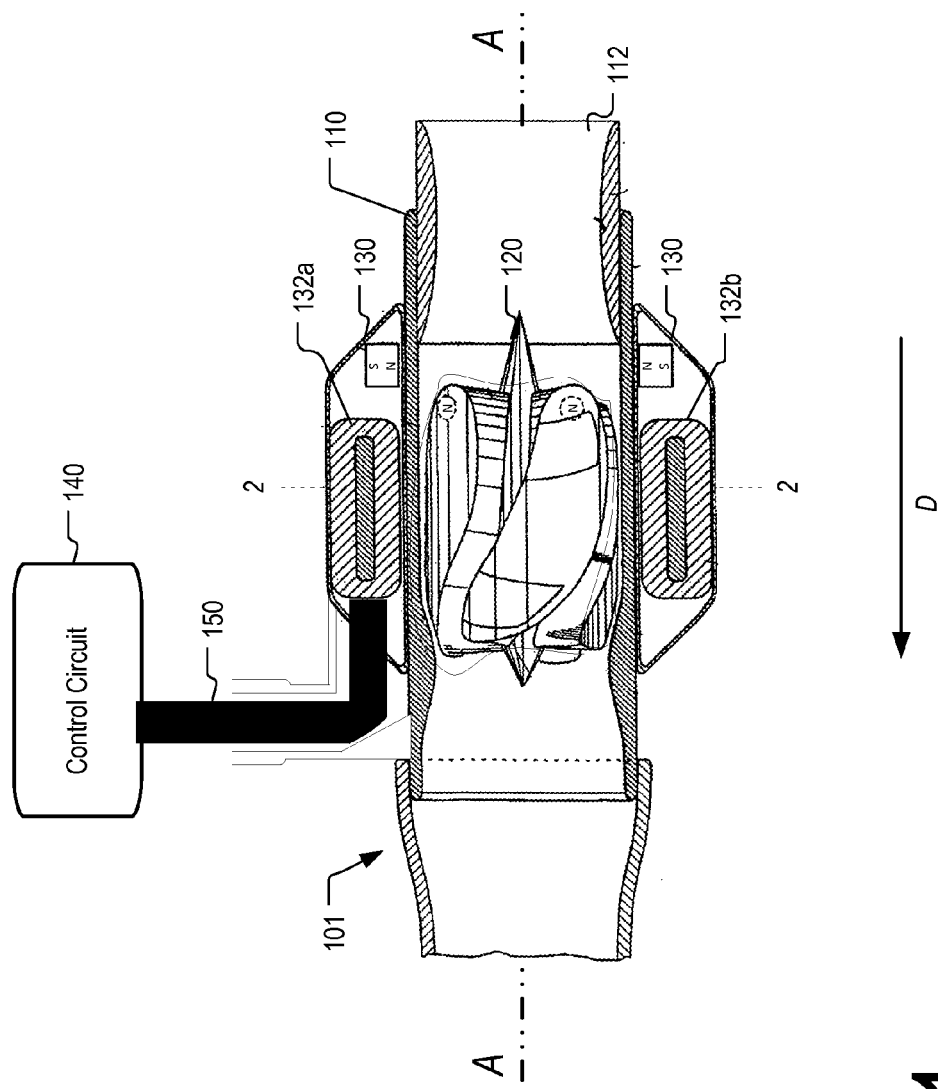
FIG. 1 is a schematic, partially sectional view of a blood pump system in accordance with one embodiment of the invention
Figure 2:
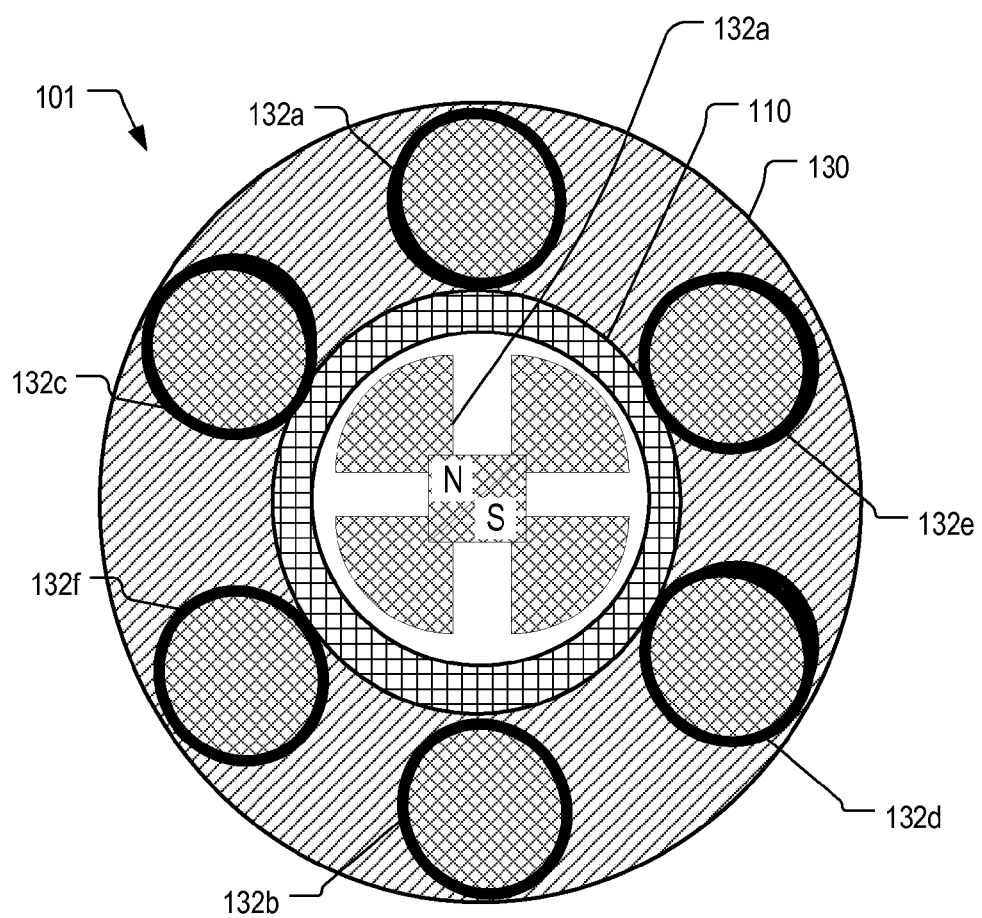
FIG. 2 is a diagrammatic sectional view taken along line 2-2 in FIG. 1.
Figure 3:
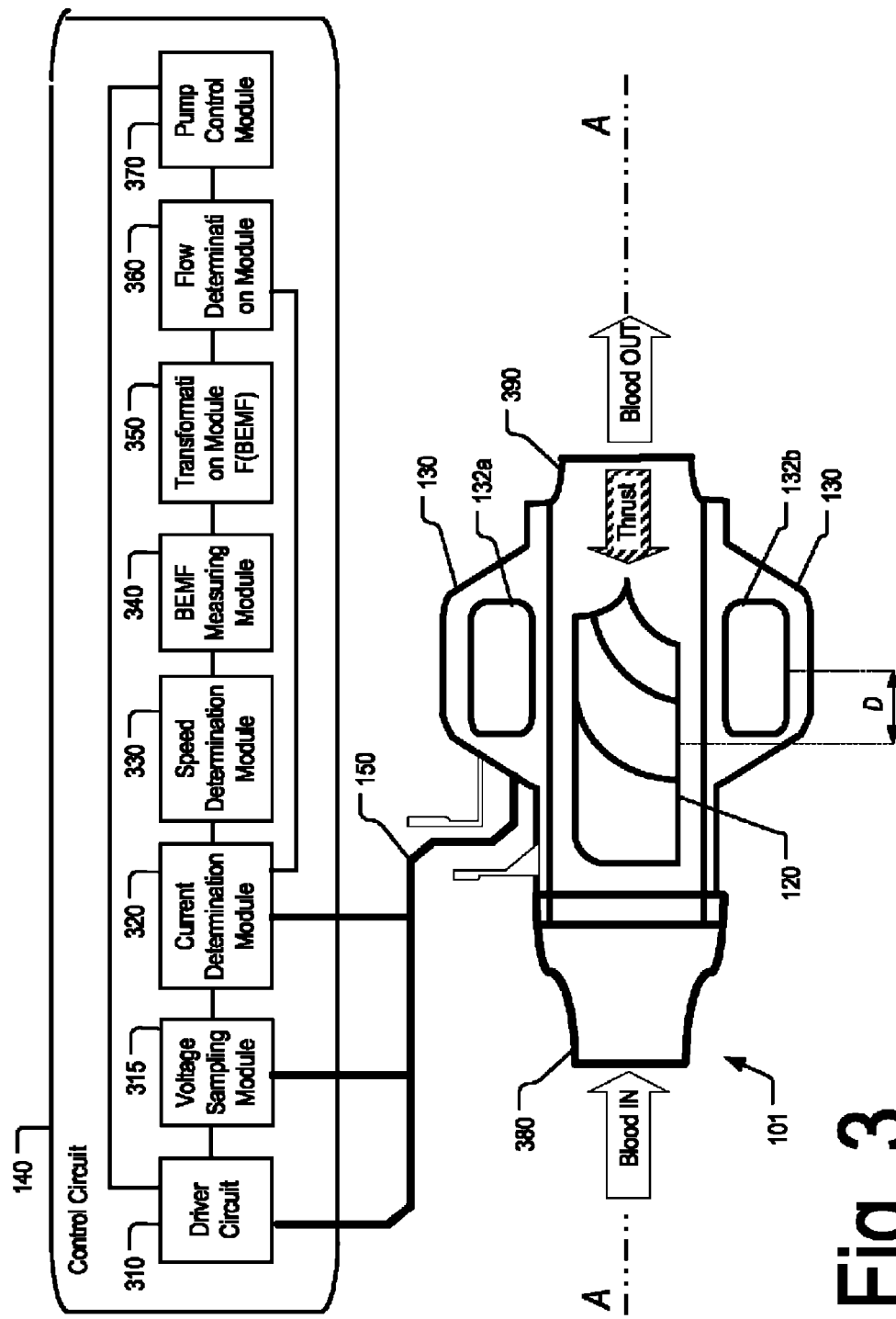
FIG. 3 is a partially functional block diagrammatic, partially sectional view of the blood pump system of FIG. 1.

FIGS. 1-3 depict a blood pump system 100 in accordance with one embodiment of the invention. The blood pump system 100 according to this embodiment includes a control circuit 140 connected via a cable feed 150 to a blood pump 101. The blood pump 101 includes a housing 110 defining a bore 112 having an axis A. A rotor 120 is disposed within the bore. The rotor 120 has a permanent magnetization with flux direction perpendicular to the axis of the bore. The rotor constitutes an impeller configured to push blood in a downstream direction D parallel to the bore 112 when the rotor is turning.

The pump also includes a stator 130. The stator includes coils 132a-e (FIG. 2) connected in a WYE or delta configuration and placed around the circumference of the housing 110. The coils are arranged in pairs diametrically opposed to one another. Thus, coils 132a and 132b form one pair, coils 132c and 132d form another pair, and coils 132e and 132f form another pair. When the coils are driven using a 3-phase current, they provide a magnetic field directed transverse to the bore axis and which rotates around the axis. The magnetic field will interact with the magnetic field of the rotor 120 causing the rotor to turn. In operation, the rotor 120 may be suspended within the bore 112 by magnetic forces, hydrodynamic forces, or both in combination. Desirably, these forces support the rotor so that it does not contact housing 110 during normal operation. Further details about suspended-rotor blood pumps, such as the pump 101, are provided in U.S. Published patent application No. 20070100196, entitled "Axial Flow Pump with Multi-Grooved Rotor," disclosure of which is incorporated herein by reference.

The control circuit 140 comprises driver circuit 310, current determination module 320, and speed determination module 330. BEMF measuring module 340, transformation module 350, flow determination module 360, and pump control module 370. The modules are depicted and discussed with reference to their individual functions. One or more of the modules 310-270 may be implemented using software operating in a computer system including a general-purpose or special purpose processor, in digital circuitry, or in using analog circuitry.

The driver circuit 310 is an electrical circuit for powering the pump 101 with a 3-phase current. Each phase of the three-phase current preferably is in the form of a generally rectangular wave including alternating off or "open-phase" periods in which power is not applied by the drive circuit and on or "closed-phase" periods during which power is applied. The periods of the various phases are arranged so that at any moment, two pairs of coils are on or closed-phase and one pair is off or open-phase. The open-phase and closed-phase periods of the various phases are arranged so that the various pairs of coils go to an open-phase state in sequence, thus creating the rotating magnetic field that actuates the rotor. Driver circuit 310 applies pulse width modulation during each on or closed-phase period. Thus, during each on or closed-phased period, the voltage applied to the pair of coils varies repeatedly between zero and a selected maximum value at a pulse modulation or chopping frequency much higher than the frequency of the rectangular waveform of the repeating closed-phase and open-phase period.

Figure 4:
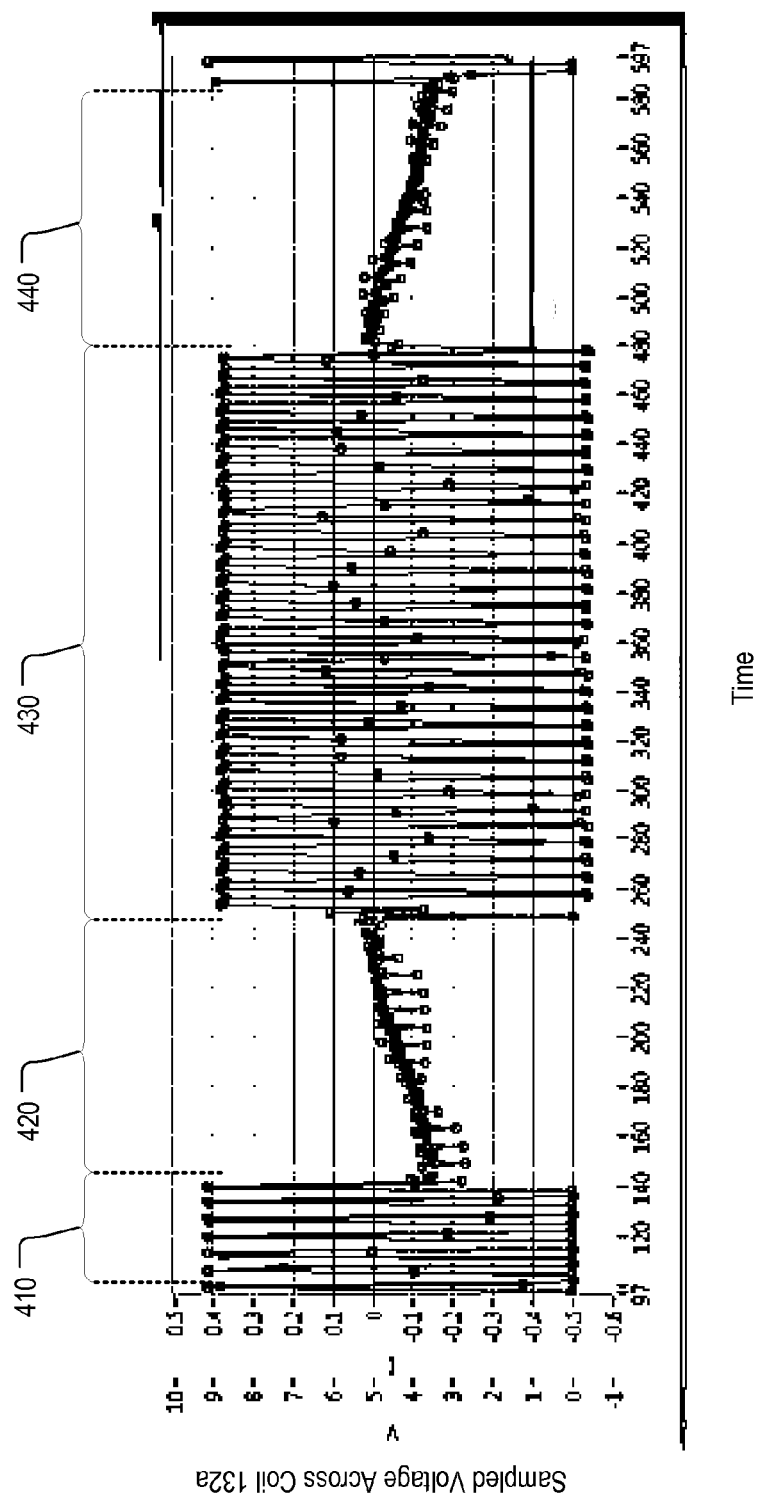
FIG. 4 depicts a plot of voltage sampled across a coil in a stator of the blood pump of FIGS. 1-3.

For example, FIG. 4 depicts the voltage across coil pair 132a and 132b. During each on or closed-phase period 410 and 430, the voltage applied by the drive circuit is repeatedly chopped or pulse-width modulated. During open-phase periods 420 and 440, the coils 132a and 132b are not energized by the driver circuit 310. During the open-phase periods, a relatively small voltage appears across coils 132a and 132b. This voltage is composed primarily of voltage induced in the coil pair 132a and 132b by the rotating magnetic rotor 120. This induced voltage is referred to as the back electromagnetic force of "BEMF." The BEMF varies in a generally sinusoidal manner; the open periods correspond to the zero-crossings of the sinusoidal variation. The voltage appearing on the coil pair during the open periods also includes some higher-frequency components representing voltage induced in pair 132a and 132b by the fluctuating pulse-width modulated currents in the other coil which are in the closed-phase or on state. During the open periods 420 and 440, the voltage across coil pair 132a and 132b is less than a given threshold (e.g., +/−0.5V).

Returning to FIG. 3, the current determination module 320 may include hardware and/or software for determining the amount of current supplied to the pump 101. For example, the current determination module may include a known resistance in series with coil pair 132a and 132b, and an analog-to-digital converter arranged to sample the voltage across the known resistance so that each such sample represents the instantaneous current passing through the coil pair, as well as an averaging circuit arranged to average these sample to provide a measure of the average current passing through the coil pair.

The control circuit further includes a voltage sampling circuit 315. The voltage-sampling circuit may include an analog-to-digital converter connected across coil pair 132a and 132b and arranged to capture successive samples of the voltage appearing across the coil pair. The voltage-sampling circuit may also include a digital filter for suppressing variations in the sampled voltage at frequencies at or above the pulse-width modulation or chopping frequency used by the drive circuit, so as to provide a filtered series of values. Alternatively, the sampling circuit may include an analog low-pass filter connected between the analog-to-digital converter and the coil pair.

A speed determination module 330 is operatively connected to the sampling circuit 315 to receive the filtered values from sampling circuit. The speed determination module is arranged to deduce the speed of rotation of the magnetic field, and hence the speed of rotation of rotor 120, from these values. For example, the speed determination module may be arranged to record the time when the voltage on coil pair 132a and 132b drops below the threshold value associated with the open-phase periods as the beginning of an open-phase period, and to calculate the interval between the beginnings of successive open-phase periods. The speed of rotation is inversely proportional to this time.

The BEMF measuring module 340 is also connected to receive the stream of sampled voltage values from sampling circuit 315, and to record the filtered voltage values during the open-phase periods. These filtered values represent the BEMF generated by the pump. Transformation module 350 is connected to BEMF measuring module 340. The transformation module processes the data collected by the BEMF measuring module 340 to determine a value of a function of the BEMF. The function is referred to herein as F(BEMF). F(BEMF) may be rate of change of the BEMF with respect to time during each open-phase period, i.e., the absolute value of the slope of the BEMF versus time. Like the BEMF measuring module 340, the transformation module 350 may also be implemented using hardware and/or software.

The flow determination module 360 may include hardware and/or software for determining the rate at which blood is impelled by the pump 101. The flow determination module is operatively connected to current determination module 320, speed determination module 330 and transformation module 350 so that the flow determination module 360 receives values representing current, speed and F(BEMF). The flow determination module is arranged to determine the flow rate from the pump based on this information as further discussed below. Pump control module 370 is operatively linked to flow determination module 360 so that the pump control module 370 receives values representing the flow rate from the flow determination module. The pump control module is also linked to driver circuit 310. The pump control module is arranged to determine a desired pump speed based, at least in part, on the flow rate and to command driver circuit 310 accordingly. Thus, the pump control module can control the pump 100 based on the blood flow rate determined by the flow determination module 370 as further discussed below.

In operation, the control circuit 140 powers the pump 101, via the driver circuit 310, thereby causing the rotor 120 to spin. As the rotor 120 spins, blood enters the pump 101 through the inflow end 380 after which the blood is impelled by the rotor 120 from the outflow end 390. As the blood passes through the pump 101, it imparts a thrust on the rotor 120. The magnitude of this thrust is related to the flow rate of blood through the pump.

As discussed above, the rotor 120 is held in position by magnetic and hydrodynamic forces. However, these forces do not hold the rotor with infinite rigidity. Therefore, thrust imparted to the rotor 120 causes the rotor 120 to move by a displacement distance D towards the inflow end 380. For at least some range of thrust values, distance D is related to the magnitude of the thrust and, thus, related to the blood flow rate. Distance D is greatly exaggerated in FIG. 3 for clarity of illustration; in practice, distance D is small in comparison to the dimension of the rotor and pump. Axial displacement of rotor 120 also changes the alignment between the rotor and the coils 132 of the pump. This alters the magnetic interaction between the rotor and the coils of the stator, and thus alters the BEMF. The effect of this alteration will depend, inter alia, on the alignment between the rotor and the coils under zero-thrust conditions and on the configuration of the rotor and the coils. However, for any particular pump operating at a particular speed with blood of a particular viscosity, the effect is repeatable and predictable. The relationship between BEMF and flow rate at one pump speed and blood viscosity for the pump of FIGS. 1-3 is shown by curve 620 in FIG. 6. In the particular embodiment of FIGS. 1-3, the BEMF increases with increasing blood flow rate at least in the range between zero and a flow rate T. Although the present invention is not limited by any theory of operation, it is believed the thrust on the rotor is a composite of reaction components directed upstream toward the inlet end of the pump and viscous components directed downstream toward the outlet end. At zero flow, the reaction components predominate and thus the thrust is directed upstream. As the flow rate increases from zero, the viscous components increase and thus the magnitude of the thrust decreases. As the thrust decreases, distance D decreases and the rotor moves into better alignment with the coils, so that BEMF increases.

Figure 6:
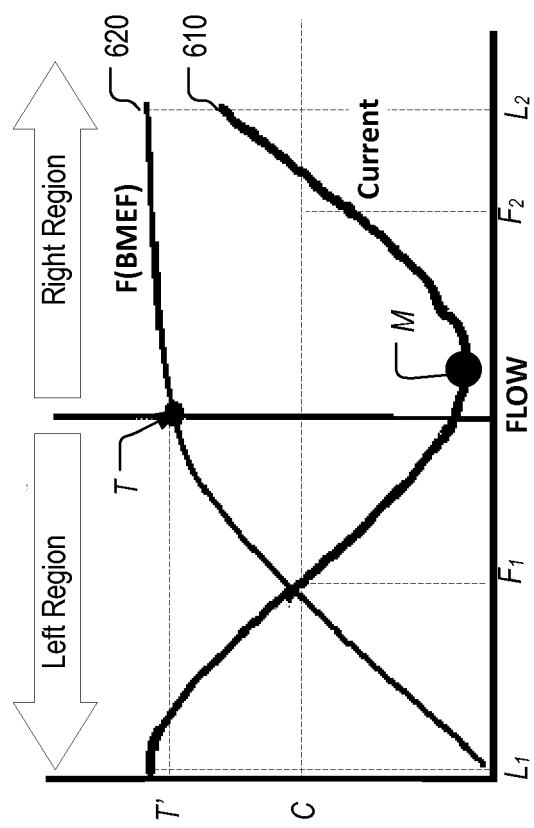
FIG. 6 is a graph depicting certain relationships in operation of the blood pump system of FIGS. 1-3.

Because F(BEMF) (the rate of change in BEMF in the open phase period) is proportional to BEMF, the same curve 620 depicts the relationship between F(BEMF) and the blood flow rate. Stated another way. F(BEMF) is a parameter related to the thrust on the rotor. The flow determination module 360 determines the flow rate of blood through the pump based in part on this parameter as further explained below. As also shown in FIG. 6, the current consumed by the pump also varies with flow rate. Curve 610 depicts the variation of current with flow rate at a particular pump operating speed. The flow determination module 360 uses both current and F(BEMF) to determine the flow rate. In brief, the flow determination module uses the value of F(BEMF) and the relationship between F(BEMF) to derive an initial estimate of flow rate. If this initial estimate indicates that the flow rate is below a value M referred to herein as the "fiducial" value, the flow determination module uses the value of current and the relationship between current and flow rate indicated in the left region of curve 610 to determine the flow rate. If the initial estimate of flow rate indicates that the flow rate is above the fiducial value M, the flow determination module uses the value of the current and the relationship between current and flow rate indicated in the right region of curve 610 to determine the flow rate.

Figure 5:
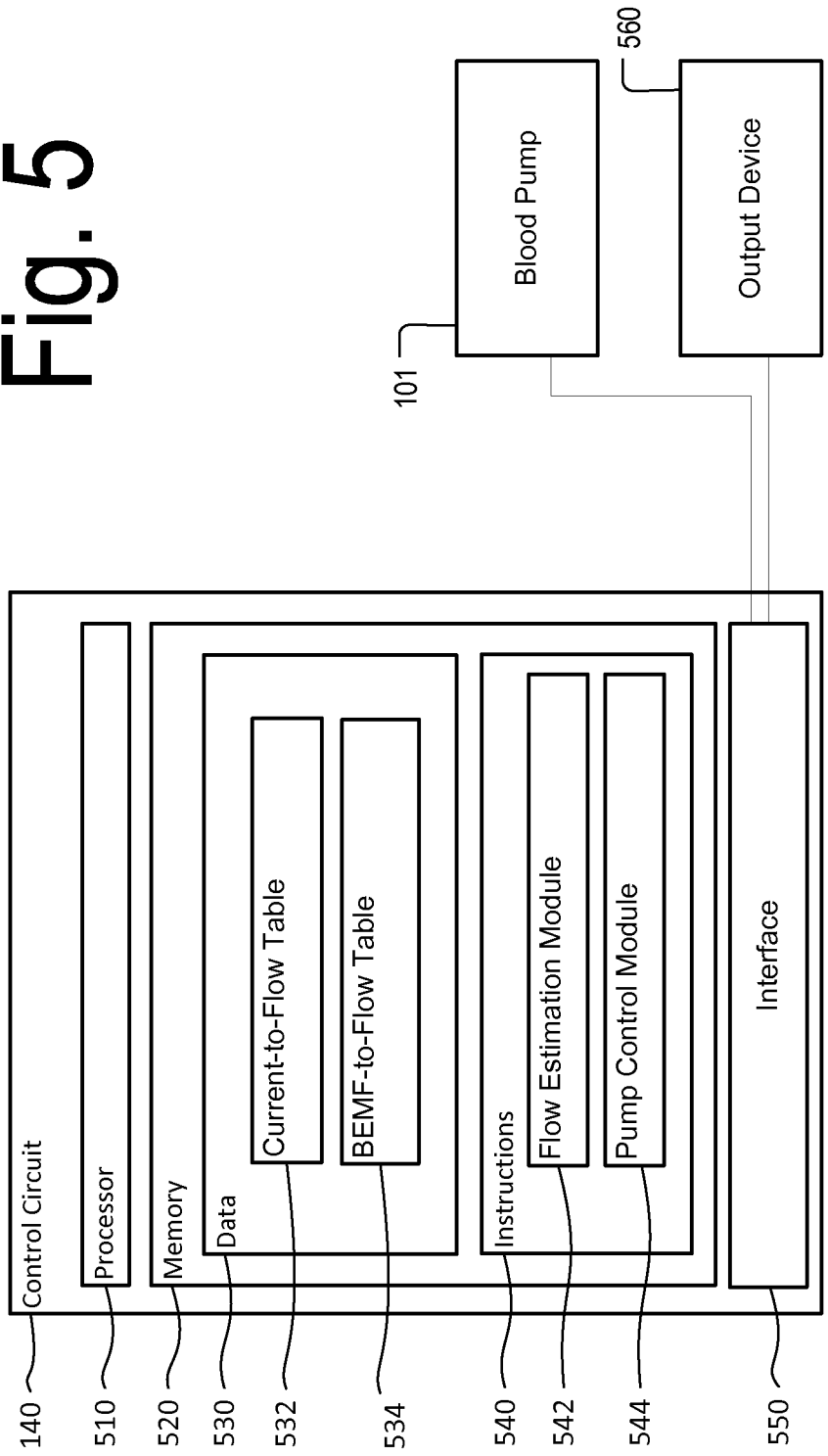
FIG. 5 is a schematic diagram showing the hardware and software used in the blood pump system of FIGS. 1-3

The various modules discussed above with reference to FIG. 3 desirably are implemented at least in part by a general-purpose processor which performs functions associated with the various modules. FIG. 5 depicts this implementation. As shown, the control circuit 140 is implemented using a processor 510, a memory 520, data 530, instructions 540, and an interface 550. Memory 520 stores information accessible by processor 510, including instructions 540 that may be executed by the processor 510. The memory also includes data 530 that may be retrieved, manipulated or stored by the processor. The memory may be of any type capable of storing information accessible by the processor, such as a hard-drive, memory card, ROM, RAM, DVD, CD-ROM, write-capable, and read-only memories. The processor 510 may be any well-known processor, such as commercially available processors. Alternatively, the processor may be a dedicated controller such as an ASIC.

Data 530 may be retrieved, stored or modified by processor 510 in accordance with the instructions 540. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data.

A current-to-flow table 532 is a tabular representation of the function 610 depicted in FIG. 6. The current-to-flow table 532 may identify one or more blood flow rates that result when a given amount of current is used to power the pump 101. An example of a current-to flow table 532 is provided as Table 1. As shown in FIG. 6, the relationship 610 between current and flow is not a single-valued function. Curve 610 illustrates, for instance, that when C amperes are used to power the pump 101, the pump 101 may impel blood at either F, L/min or F 2 L/min. In other words, the plot illustrates that in this embodiment, there is a many-to-one mapping between current and blood flow rate. As also shown by curve 610, the relationship is such that for any flow in the left region of the current-to-flow relationship, below the fiducial value M liters/minute, there is a one-to-one mapping between current and flow. At any flow above the fiducial value M liters/minute, there is a different one-to-one mapping between current and flow.

Thus, as depicted in Table 1, the current-to-flow map stores plural values of flow rate for each value of current, one associated with the left region and one associated with the right region. At a value of current corresponding to the fiducial flow rate (1.0 amps in the example of Table 1), the two values are the same; the current-to-flow table 532 indicates that when the pump 101 is powered with 1.0 amps of current, it pumps blood at the rate of 2 L/min. At a current of 1.2 amps, the blood flow rate is either 1.5 L/min or 3.0 L/min. The current-to-flow relationship varies with the speed of operation of the pump, i.e., the rotation rate of the rotor. The current-to-flow relationship also varies with viscosity of the blood. The viscosity of the blood is directly related to the hematocrit, i.e., the proportion of the blood volume occupied by red blood cells. Therefore, the current-to-flow table stores different sets of values, each associated with a range a particular pump operating speed and blood viscosity. Each such set of values includes a fiducial value M. Sets of values for other pump operating speeds and viscosities are calculated from the stored sets by interpolation. The flow calculation module selects the appropriate set of values based on the speed of operation of the pump and on a value of hematocrit or blood viscosity for the patient which has been supplied to the system from an external source through interface 550. The current-to-flow table 532 may be implemented as a file, a data structure, as part of a database, or in any other suitable form.

TABLE 1

Current-to-Flow Map

| Current | Blood Flow Rate Left Region | Blood Flow Rate Right Region |
|---|---|---|
| 1.0 amps | 2.0 L/min | 2.0 L/min |
| 1.2 amps | 1.5 L/min | 3.0 L/min |
| 1.4 amps | 1.0 L/min | 4.0 L/min |

F(BEMF)-to-flow table 534 may be a tabular representation of the function 620 depicted in FIG. 6. The F(BEMF)-to-flow table 534 identifies the flow rate of blood impelled by the pump 101 when the F(BEMF) indicates that the BEMF in coil pair 132a and 132b changes at a given rate with respect to time. The BEMF-to-flow relationship also changes with pump operating speed and viscosity, i.e., hematocrit. Therefore, table 534 includes different sets of data, each associated with a given speed of rotation of the rotor 120 and a given viscosity. Here again, values for pump operating speeds and blood viscosities not represented in the stored data are derived by interpolation.

An example of the F(BEMF)-to flow table 534 is provided as Table 2. According to this example, the BEMF-to-flow table 534 indicates that when the BEMF in the coil 132a changes at the rate of 5.5 V/s, the pump 101 impels blood at the rate of 2.5 L/min. The BEMF-to-flow table 534 may be implemented as a file, a data structure, as part of a database, or in any other suitable form.

TABLE 2

BMEF-to-Flow Map

| F (BMEF) | Blood Flow Rate (@ 10000 rpm) |
|---|---|
| 0.2 V/s | 0.75 L/min |
| 0.4 V/s | 1.5 L/min |
| 0.5 V/s | 2.0 L/min |
| 0.55 V/s | 2.4 L/min |
| 0.60 V/s | 2.5 L/min |

The data 530 may also include other tables, such as the flow-to-pressure tables described in greater detail below (e.g., FIG. 10). The data in each of the tables may be determined experimentally using the actual pump or a sample pump of similar configuration. In addition, each of the tables may be pre-loaded in the memory 520 before the pump 101 is deployed.

The instructions 540 may be instructions to be executed directly (such as machine code) or indirectly (such as scripts) by the processor. In that regard, the terms "instructions," "steps" and "programs" may be used interchangeably herein. The instructions may be stored in object code format for direct processing by the processor, or in any other computer language including scripts or collections of independent source code modules that are interpreted on demand or compiled in advance. Functions, methods and routines of the instructions are explained in more detail below. Flow estimation module 542 may include instructions for determining the blood flow rate produced by the pump 101 as further explained below, whereas pump control module 544 may include instructions for controlling the operation of the drive circuit 310 (FIG. 3) and thus controlling pump 101. The operation according to instructions 540 is further discussed below with respect to FIG. 7.

The control circuit 140 may optionally include an interface 550 which connect the control circuit 140 to an output device 560. The interface 550 may be an analog interface (e.g., audio interface) or a digital interface, such as Bluetooth. TCP/IP, 3G, and others. Where the control circuit is implemented in an implantable structure adapted to be disposed within the body of the patient, the interface 550 may include known elements for communicating signals through the skin of the patient. The output device 560, may be a speaker, a communications terminal (e.g., computer, cell phone) or any other type of device.

Although FIG. 5 functionally illustrates the processor and memory as being within the same block, it will be understood that the processor and memory may actually comprise multiple processors and memories that may or may not be stored within the same physical housing. The memory may include one or more media on which information can be stored. Preferably, the medium holding the instructions retains the instructions in non-transitory form. Some or all of the instructions and data may be stored in a location physically remote from, yet still accessible by, the processor. Similarly, the processor may actually comprise a collection of processors which may or may not operate in parallel.

Figure 7:
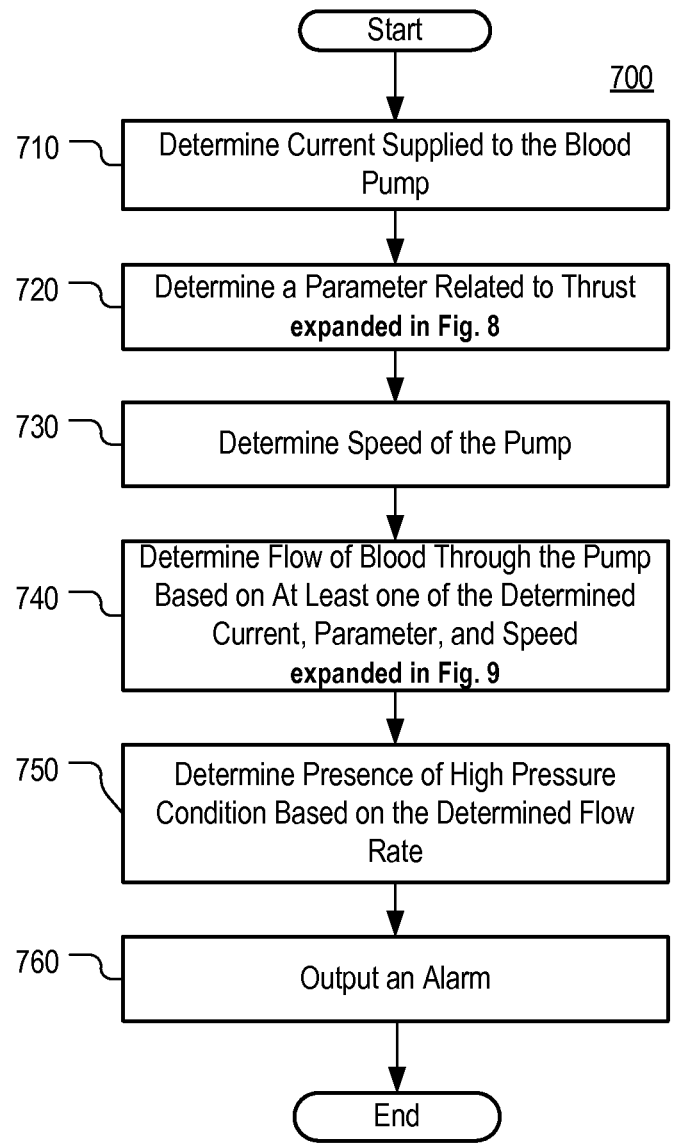
FIG. 7 depicts a flowchart of a method of operation used by the system of FIGS. 1-3.

FIG. 7 depicts a flowchart of a process 700 for determining the rate at which blood is impelled by the pump 101. At task 710, the control circuit 140 determines the amount of current that is used to power the pump 101.

Figure 8:
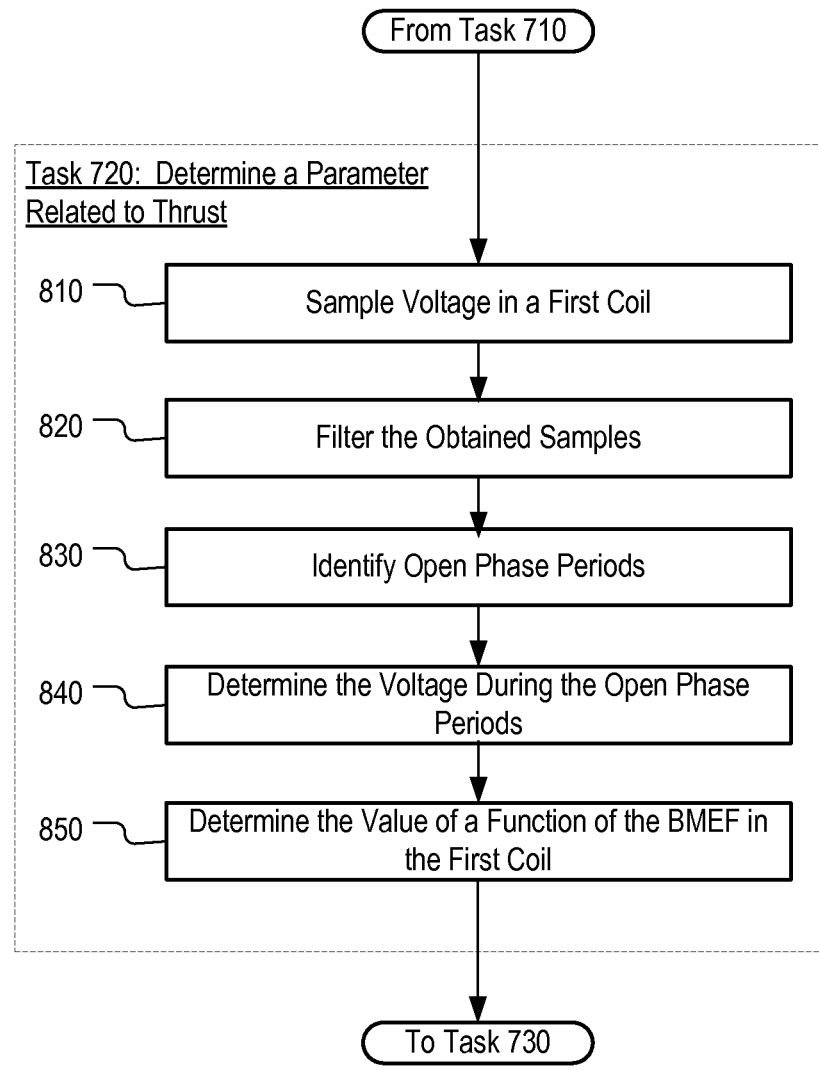
FIGS. 8 and 9 are detailed flowcharts depicting portions of the method FIG. 7.

At task 720, the control circuit determines a parameter related to thrust imparted on the rotor 120 by the flow of blood exiting the pump 101. In this embodiment, the determined parameter is the function F(BEMF), the rate of change of BEMF during the open phase periods of coil pair 132a and 132b as discussed above. FIG. 8 depicts the sub-steps of step 720. To determine the F(BEMF), the control circuit 140 first samples voltage across the coil pair 132a and 132(b). In one embodiment, for example, the sampling frequency may be 200 kHz (Task 810). The samples may then be filtered using an average filter. For example, the filter may be specified as Vout[i]=K*Vin[i]+(1−K)*Vout[i−1], where 0≤K≤1 (Task 820). The control circuit 140 then identifies an open phase period. In some aspects the open-phase period based on the voltage levels of the sampled signal being under a predetermined threshold (Task 830). Once one or more open-phase periods are identified, the control circuit 140 determines the voltage across the coil 132a during the identified open-phase periods. The determined voltage is the BEMF (Task 840). The control circuit calculates F(BEMF), the rate of change in BEMF from the BEMF values during the open-phase periods (Task 850). The rate of change may be measured using any number of voltage samples (e.g., 2, 20, 200) taken at any sampling frequency (e.g., 200 kHz). Desirably, calculation of F(BEMF) occurs in real time.

At task 730, (FIG. 7) the control circuit 140 determines the speed of rotation of the rotor 120. As discussed above the control circuit samples voltage across the coil pair 132a and 132b, identifies open-phase periods in which the voltage appearing across the coil is less than a threshold voltage, and determines the number of the open-phase periods per unit time or, equivalently, the time between successive open-phase periods for a particular coil. The control circuit determines the speed based on this measurement. The greater the number of open-phase periods per unit time, or the lesser the time between successive open-phase periods, the faster the speed.

At task 740, the control circuit 140 determines the rate at which blood is impelled by the pump 101 based on the parameter related to thrust determined at task 720.

Figure 9:
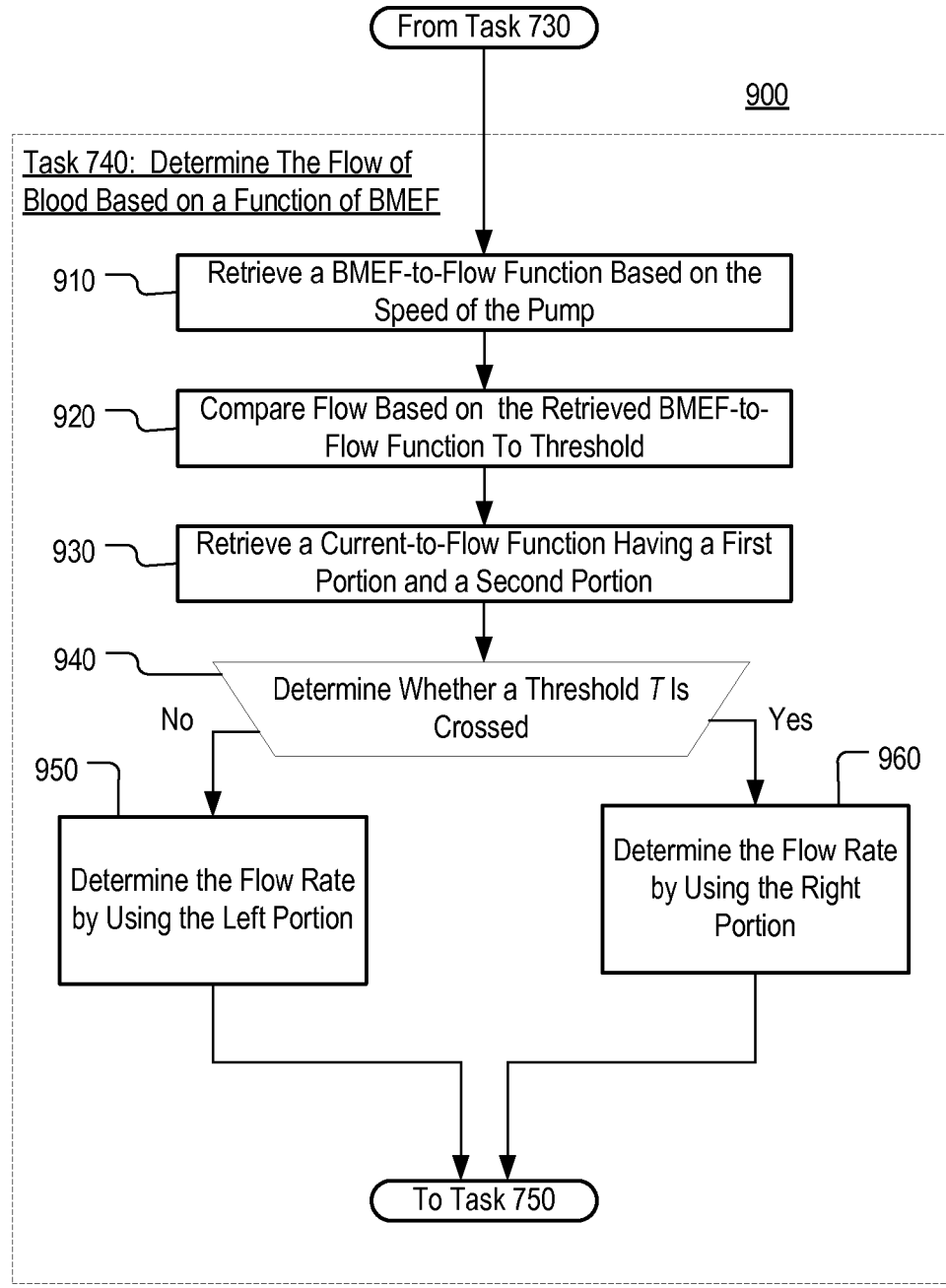

The tasks included in task 740 are shown in greater detail in FIG. 9. At task 910, the control terminal retrieves a function that maps the BEMF slope to a blood flow rate, i.e., F(BEMF)-to-flow table 534 (FIG. 5 and Table II, above), for the speed at which the pump is operating. At task 920, the control circuit 140 determines whether the blood flow rate associated with the value of F(BEMF) is above or below a predetermined threshold value T associated the function 620 (FIG. 6). As depicted in FIG. 6, the threshold value T is a value which is the same, or approximately the same, as the blood flow rate M at the fiducial point which separates the left and right regions of the current-to-flow rate relationship 610 at the speed at which the pump is operating. The control circuit may use F(BEMF)-to-flow table 534 (Table II above) and retrieve the value of flow corresponding to the value of F(BEMF). In this process, the control circuit may interpolate between stored values using standard interpolation techniques. The circuit then compares the retrieved value of flow to the threshold T. and determines whether the value of flow indicated by F(BEMF) is above or below the threshold T. In the alternative, because there is a one-to-one mapping between F(BEMF) and flow, the same step can be performed by simply comparing F(BEMF) to a threshold value of F(BEMF) indicated T' (FIG. 6) which corresponds to the threshold value of flow T. If this alternative method is used, the memory may not store the entire F(BEMF)-to-flow table 534, but instead may simply store a value T' associated with each operating speed.

At task 930, the control circuit 140 retrieves the function 610 that maps an amount of current supplied to the pump 101 to blood flow rate that is generated by the pump 101, i.e., the current-to-flow table 532 (FIG. 5 and Table 1, above).

At task 940, the control circuit 140 branches to one of two different paths. If the threshold comparison (task 920) indicates that F(BEMF) is below threshold T (FIG. 6) task 950 is executed. Otherwise, the control circuit 140 executes task 960.

At task 950, the control circuit 140 determines the rate at which blood is impelled by the pump 101 based on the left portion of the function 610. To evaluate the left portion of the function 610, the control circuit 140 may use the value of current as an index and retrieve the corresponding value of flow from the entries in the current-to-flow table 532 (and Table 1, above) that pertains to the left portion. Alternatively, the control circuit 140 may obtain two or more blood flow rate values that correspond to the same amount of current and then select the smallest one. In either process, standard interpolation techniques can be used when the value of current falls between stored values.

At task 960, the control circuit 140 determines the rate at which blood is impelled by the pump 101 based on the right portion of the function 410. To evaluate the right portion of the function 610, the control circuit 140 may use the value of current as an index and retrieve the corresponding value of flow from the entries in the current-to-flow table 532 (and Table 1, above) that pertain to the right portion. Alternatively, the control circuit 140 may obtain two or more blood flow rate values that correspond to the same amount of current and then select the largest one. In either process, standard interpolation techniques can be used when the value of current falls between stored values.

At task 750 (FIG. 7), the control circuit 140 determines whether a high pressure condition is present in the pump 101 based on the determined flow rate. For example, the control circuit may correlate the determined flow rate with a differential pressure value representative of the differential pressure across the pump. A differential pressure value greater than a predetermined threshold pressure value may be indicative of a high pressure condition across the pump. In some instances, the control circuit, upon detection of the high pressure condition, may issue an alarm signal (task 760, FIG. 7) through the interface 550 (FIG. 5) to output device 560, so that the patient or a caregiver is notified of the problem. In other instances, issuance of an alarm signal may be delayed until the control circuit determines that the high pressure condition cannot be cleared using one or more preprogrammed recovery techniques. Controlling operation of the pump in response to the detected high pressure condition, including said recovery techniques, is described in greater detail in FIG. 12.

With respect to correlating the determined flow rate with a differential pressure value, at a given viscosity and pump operating speed, there is a predetermined relationship between flow rate and pressure drop across the pump. For any given pump design, this relationship can be found by experiment and represented in tables of data. Thus, the system can calculate pressure drop from flow rate and report pressure drop in lieu of flow rate, or in addition to flow rate.

Figure 10:
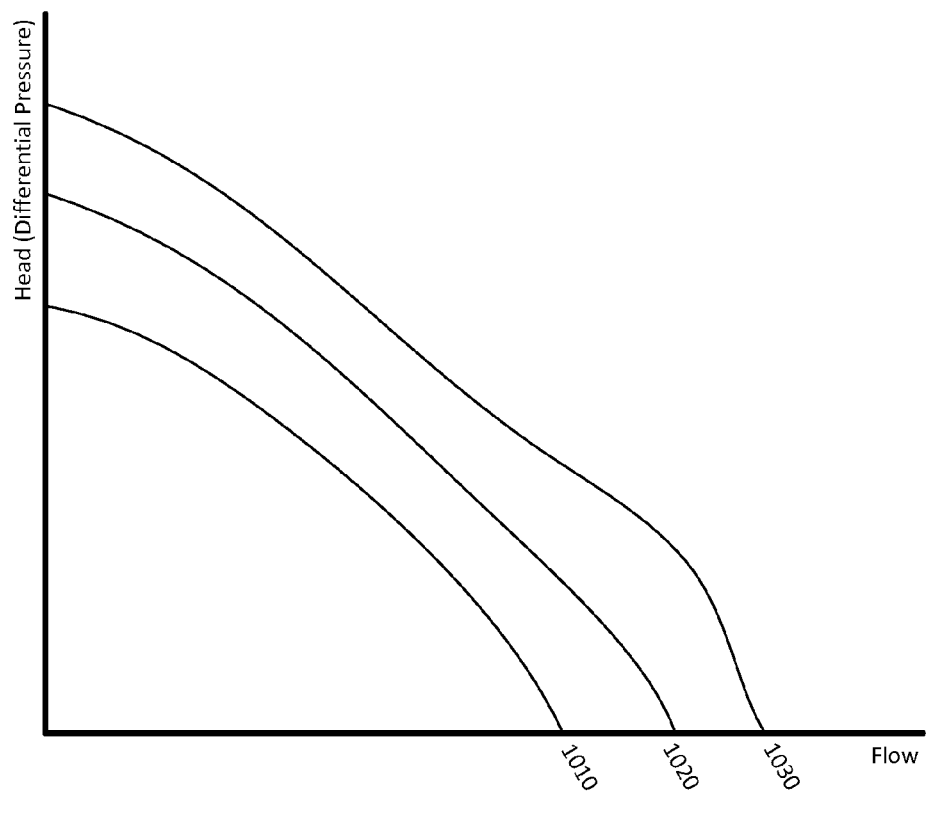
FIG. 10 is a graph depicting relationship between differential pressure and flow rate in the blood pump system of FIGS. 1-3.

The example data table 1000 of FIG. 10 depicts a relationship between flow rate and pressure drop (or differential pressure) across the pump for an example blood pump of the present disclosure. Data table 1000 includes three data curves 1010, 1020 and 1030, each representative of the known relationship at a given pump operating speed (14 kRPM, 16 kRPM and 18 kRPM for each of the data curves 1010, 1020 and 1030, respectively). Other data tables may include more data curves conveying a flow rate-to-differential pressure relationship for a range of speeds at which the pump is capable of operating based on the pump's characteristics (e.g., a range of speeds between about 14 kRPM and 18 kRPM, between 14 kRPM and 22 kRPM, etc.).

Figure 11:
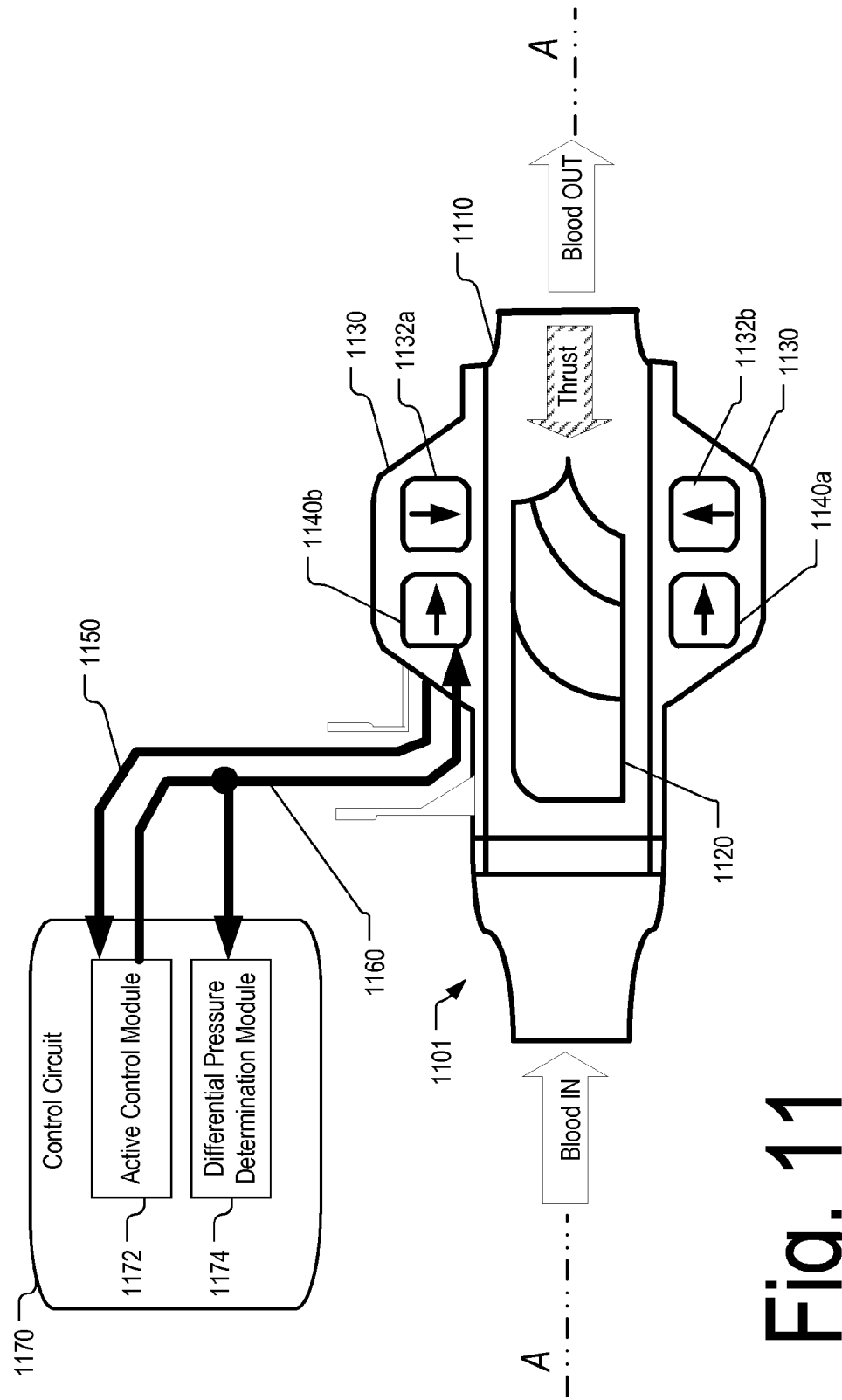
FIG. 11 is a partially block diagrammatic, partial sectional view of a blood pump system in accordance with another embodiment of the invention.

A blood pump system 1100 (FIG. 11) in accordance with yet another embodiment of the invention incorporates an active control system comprising an active control module which exerts an axial force on the rotor to counteract the effects of thrust on the rotor and maintain the rotor in a substantially constant axial position. Further examples of active control systems are provided in pending U.S. Publication No. 2011/0237863, entitled "Magnetically Levitated Blood Pump With Optimization Method Enabling Miniaturization."

System 1100 comprises a pump 1101 and control circuit 1170. The pump 1101 comprises a rotor 1120 disposed within housing 1110 and actuated by a stator 1130. The rotor 1120 comprises coils 1130. Unlike the pump 101 (FIG. 1), the pump 1101 (FIG. 11) also comprises electromagnets 1140*a-b* for producing a magnetic field which exerts an axial force on rotor 1120 that is opposite in direction and similar in magnitude to the thrust imparted on the rotor 1120 by the flow of blood impelled by the pump 1101. The force produced by the electromagnets balances out the thrust and allows the rotor 1120 to remain in place.

Control circuit 1170 may include an active control module 1172 and differential pressure determination module 1174.

The active control module 1172 may receive input signal(s) 1150 and outputs control signal(s) 1160. In this example, the control signal 1160 controls the magnitude of the magnetic field produced by at least one of the electromagnets 1140*a-b*. The control signal 1160 may be a digital directed to a controller that operates the electromagnets 1140*a-b*, an analog current used to power the electromagnets 1140*a-b*, or any other signal. Because the control signal 1160 sets the magnitude of the magnetic field of the electromagnets 1140*a-b*, which is used to offset the thrust imparted on the rotor 100 by the flow of blood output by the pump 101, the control signal bears a direct relationship to the thrust.

The signal 1160 constitutes another example of a parameter related to thrust and it may be used to determine blood flow rate. The differential pressure determination module 1174 may first determine the blood flow rate produced by the pump 1101 by receiving the control signal 1160 and matching it to a corresponding blood flow rate, and then matching it to a further corresponding differential pressure value. For example, one table may be stored in a memory of the control circuit 140 to relate different values for the control signals 1140 to blood flow rate, and another table may be stored in the memory to relate different values of blood flow rate to differential pressure across the pump. Here again, the table may include different sets of data for different pump operating speeds and blood viscosities. The differential pressure determination module 1174 may use the table to match the value of the control signal 1160 to a corresponding differential pressure value.

In still other arrangements, thrust can be measured directly. For example, if the pump includes a bearing which retains the rotor against axial movement, the bearing may incorporate a piezoelectric element or other force transducer. The signal from the force transducer, or a function of the signal, may be used as the parameter related to thrust.

In the embodiment discussed above with reference to FIGS. 1-9, the parameter F(BEMF) related to thrust is used to select a portion of the current-to-flow relationship 610 (FIG. 6), i.e., the left or right portion of the curve. In a variant of this approach, the system can determine flow directly from F(BEMF) using the F(BEMF)-to-flow table 534 (FIG. 5 and Table 2, above) whenever the value of flow indicated by F(BEMF) is below the threshold value T, and determine the flow based on the right portion of the current-to-flow relationship 610 when the value of flow indicated by F(BEMF) is above the threshold value T. In the particular system discussed above with reference to FIGS. 1-9, the relationship between F(BEMF) and flow is such that for values above the threshold, the slope of curve 620 becomes relatively small. In this region, a large change in flow corresponds to only a small change in F(BEMF). This makes it difficult to determine the flow accurately from F(BEMF). However, in other systems having different rotor and coil configurations, the relationship between F(BEMF) and flow provides more substantial variation of F(BEMF) per unit change in flow rate over the entire range of flow rates to be monitored. In those cases, the flow rate can be determined based solely on F(BEMF), without reference to the current used by the pump. Likewise, where another parameter related to thrust is employed, the determination of flow rate can be based solely on such other parameter.

The control circuit 140 need not store relationships between a parameter such as F(BEMF) and flow or between current and flow in the form of lookup tables as discussed above. The control circuit may retrieve and evaluate a formula that models the rate at which blood is impelled by the pump as a function of the parameter related to thrust, e.g., a formula for the function 620 (FIG. 6). Likewise, the control circuit may retrieve and evaluate a formula for the current-to-flow relationship, e.g., a formula of the function 610. One or more similar formulas may be stored and retrieved for modeling and evaluating the flow-to-pressure relationship, e.g., a formula of the flow-to-pressure curves 1010, 1020, and 1030 (FIG. 10).

Figure 12:
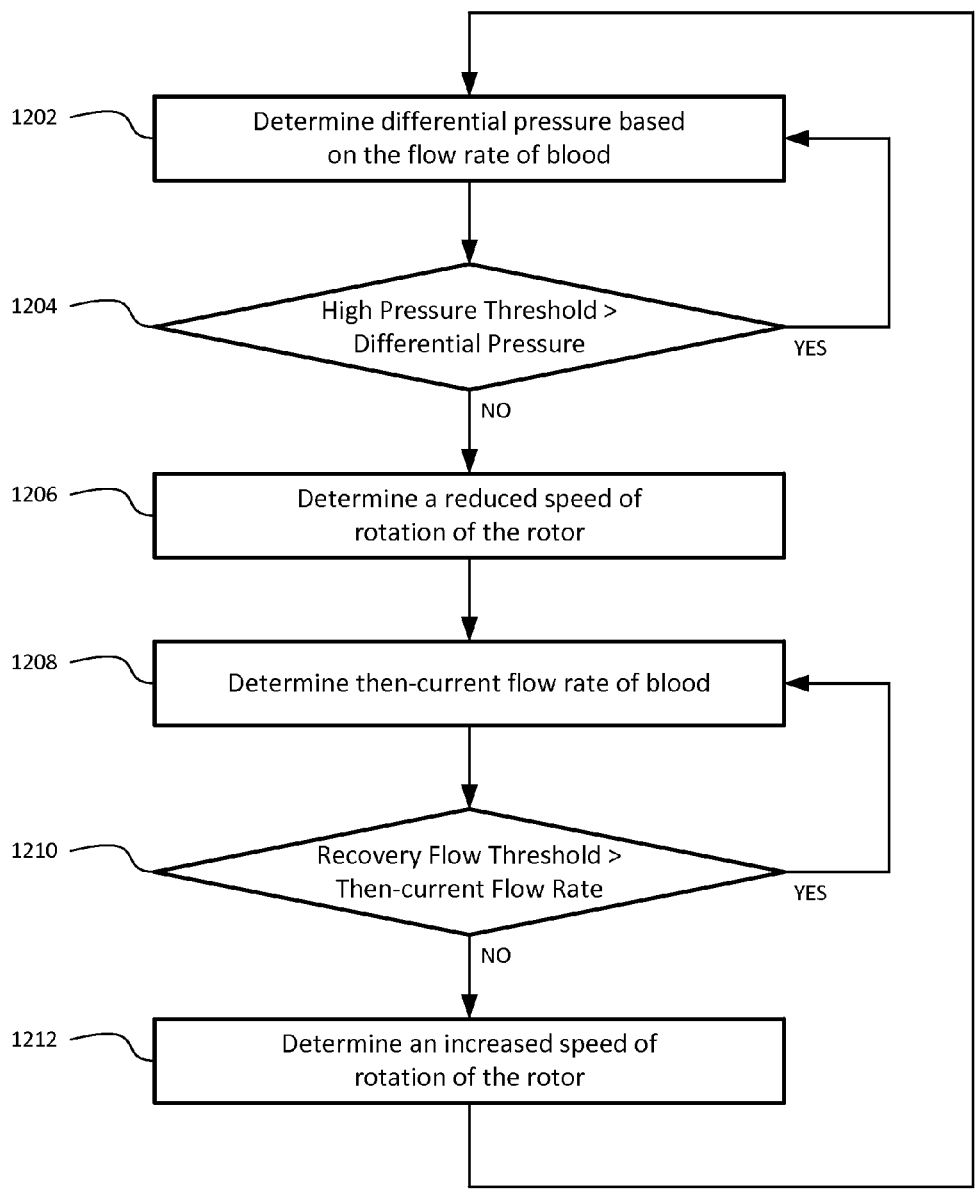
FIG. 12 depicts a flowchart of another method of operation used by the system of FIGS. 1-3.

A method of operation to regulate pressure buildup across the pump, according to one embodiment of the disclosure, is shown in the flow diagram 1200 of FIG. 12. The flow diagram 1200 begins with the pump operating at its normal operating speed (e.g., 18 kRPM) as its initial speed. At task 1202 of FIG. 12, the control circuit of the pump determines the differential pressure across the pump based on the determined flow rate of blood. This determination may be performed using data stored in the memory of the control circuit, such as a data table correlating flow rate to differential pressure. As described above, the relationship between flow rate and differential pressure may vary based on the speed of rotation of the rotor. Thus, the determination of differential pressure may further be based on the speed of rotation of the rotor.

At task 1204, the control circuit compares the determined differential pressure value to a predetermined threshold pressure value. The predetermined threshold pressure value may be stored in the memory of the control circuit. A differential pressure value greater than the threshold pressure value may be indicative of unwanted pressure buildup across the pump, and thus may further be indicative that the control circuit should take further action to relieve or clear the pressure buildup. If the differential pressure value is determined to be less than the threshold pressure value, then no further action is necessary by the control circuit to regulate the differential pressure across the pump, and operations continue at task 1202 where the differential pressure value is again determined (i.e., repeatedly monitored).

If the differential pressure value is determined to be greater than or equal to the threshold pressure value, then the control circuit takes action to regulate the pressure across the pump, and operations continue at task 1206 where the control circuit determines a reduced speed of rotation of the rotor. The reduced speed may be a preselected reaction speed (e.g., 14 kRPM), and may be stored in the memory of the control circuit. The reaction speed is selected to sufficiently ease pressure buildup across the pump.

As the pump operates at the reduced speed, the flow rate gradually increases, resulting in a gradual drop in pressure across the pump. At task 1208, the control circuit determines the then-current flow rate of blood. At task 1210, the determined flow rate is then compared to a predetermined recovery flow threshold. The predetermined recovery flow threshold may be stored in a memory of the control circuit. A flow rate greater than or equal to the recovery flow threshold may indicate that the pressure across the pump has been reduced to the extent that operation of the pump may resume at its normal (or previous) operating speed (i.e., speed of operation at tasks 1202 and 1204). Conversely, a flow rate less than the recovery flow threshold may indicate that the pressure across the pump has not yet been reduced. If the flow rate is determined to be less than the recovery flow threshold, then no further action is taken by the control circuit, and operations continue at task 1208 where the flow rate is again determined (i.e., repeatedly monitored).

If the flow rate is determined to be greater than or equal to the recovery flow threshold, then the control circuit takes action to resume normal operation of the pump, and operations continue at task 1212 where the control circuit determines an increased speed of rotation of the rotor. In one example, the increased speed of rotation may be the normal operating speed (i.e., the speed at which the pump operated at tasks 1202 and 1204). In other examples, the increased speed of rotation may be one of a series of incremental speeds between the reaction speed and the normal operating speed. In the example of FIG. 12, the increased speed is the normal operating speed, and operations then continue at task 1202, where the control circuit continues to regulate operation of the pump, thereby ensuring that excessive pressure does not build up across the pump.

Figure 13:
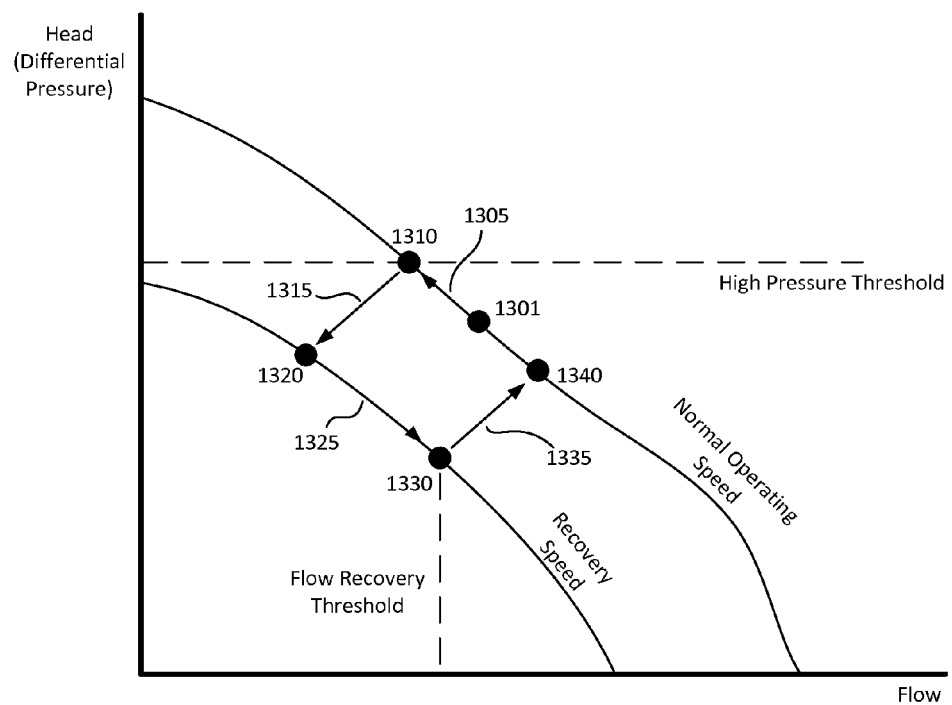
FIG. 13 is graphical representation of an embodiment of the method depicted in FIG. 12.

The operations of flow diagram 1200 are further illustrated in FIG. 13 with respect to the operation points at which the pump is set by the control circuit, as measured by the above described flow rate and differential pressure determinations. Operation of the pump begins with the rotor at the normal operating speed. For any given determined flow rate of the pump, the differential pressure across the pump may be determined using the normal operating speed curve. Under normal operating conditions, with no blockage or suction condition, the pump runs at a point between points 1340 and 1310 (e.g., point 1301). If pressure builds up across the pump (arrow 1305), the flow drops and the pressure correspondingly increases until the pump is operating at point 1310. At this point, the determined differential pressure equals the threshold pressure value, and the control circuit reduces the operating speed of the rotor to the reaction speed (arrow 1315) such that the pump operates at point 1320 having a reduced differential pressure. The reduction in speed causes an immediate reduction in the flow rate. The reduced flow rate may clear the problem which created the pressure buildup. In this case, when the rotor is maintained at the reaction speed, the pressure across the pump continues to drop while the flow rate increases (arrow 1325). When the pressure drops enough for the determined flow rate to reach the recovery flow threshold, at point 1330, the control circuit increases the operating speed of the rotor back to the normal operating speed (arrow 1335) such that the pump operates at point 1340. If the pressure again builds up to point 1310, the above described operations may repeat.

As described above, the control circuit may transition the rotor from the reaction speed to the normal operating speed in several small increments (e.g., 1 kRPM increments). The control circuit may hold the rotor at a given speed for a predetermined amount of time (e.g., about 10 seconds) before initiating the next increment. The delay in incrementing the rotor speed gives the control circuit an opportunity to evaluate whether increasing the rotor speed has triggered a high pressure condition, as well as to evaluate the highest speed that may be maintained without triggering a high pressure condition.

The control circuit may evaluate the flow rate of blood at the pump for each increment in order to determine whether to increase the rotor speed to the next increment. For example, if increasing the rotor speed causes the flow rate to drop below the recovery flow threshold (which in turn is indicative of increased differential pressure), then the control circuit determines not to further increment the rotor speed. Additionally, each rotor speed increment may be associated with different flow recovery threshold value, as depicted by the dashed flow recovery threshold line of FIG. 13 and in Table 3 below. For any given rotor speed, the control circuit may wait for the flow rate of blood in the pump to increase to a corresponding threshold before further incrementing the speed of the rotor. After the waiting period, the control circuit checks whether the flow rate has increased. If it has, then the control circuit increases the speed. If not, the control circuit holds the speed. Thus, checking the flow rate may be repeatedly performed, and the flow recovery threshold may be repeatedly updated to the corresponding threshold value (e.g., Table 3), until the rotor speed returns to the normal operating speed.

TABLE 3

Speed-to-Flow Recovery Threshold Map

| Speed (RPM) | Flow Recovery Threshold (ml/min) |
| --- | --- |
| 14200 | 1.1 |
| 14400 | 1.2 |
| 14600 | 1.3 |
| 14800 | 1.4 |
| 15000 | 1.5 |
| 15200 | 1.6 |
| 15400 | 1.7 |
| 15600 | 1.8 |
| 15800 | 1.9 |
| 16000 | 2.0 |
| 16200 | 2.1 |
| 16400 | 2.2 |
| 16600 | 2.3 |
| 16800 | 2.4 |
| 17000 | 2.5 |
| 17200 | 2.6 |
| 17400 | 2.7 |
| 17600 | 2.8 |
| 17800 | 2.9 |

In the event that an attempt to transition the pump from the reaction speed to the normal operation speed (hereinafter, a "recovery attempt") fails due to detection of a high pressure condition, the control circuit may set the rotor speed back to the reaction speed. The control circuit may then initiate another recovery attempt as soon as the flow rate equals or exceeds the recovery flow threshold corresponding to the reaction speed. After one or more failed recovery attempts (e.g., one, two, four recovery attempts, etc.) due to repeated detection of high pressure conditions, the control circuit may set and maintain the rotor speed at a safe operational speed for a predetermined hold time (e.g., 15 minutes) before initiating another recovery attempt. In some examples, the safe operational speed may be the reaction speed. Alternatively, the safe operational speed may be the highest operating speed achieved by the pump during the previous recovery attempt or attempts without triggering a high pressure condition. For instance, if a high pressure condition is triggered each time the rotor is set to a speed of 17 kRPM, then the safe operation speed may be the increment below 17 kRPM (e.g., 16 kRPM). The above process of repeatedly attempting recovery before setting the rotor speed to a safe operational speed for the hold time if hereinafter termed a retry cycle.

In one example embodiment, the control circuit may be programmed to attempt a predetermined number of retry cycles (e.g., one, two, four retry cycles, etc.). If after the predetermined number of retry cycles the control circuit still cannot set the pump to the normal operating speed without triggering a high pressure condition, then the control circuit may cease initiating any further recovery attempts. The control circuit may then issue an alarm (task 760, FIG. 7) indicating that the pump is not functioning properly and/or that the patient requires medical attention. The control circuit may also maintain the rotor speed at the safe operating speed until such operation is manually overridden, such as by a clinician.

The number of recovery attempts and/or retry cycles initiated by the control circuit may be logged by a counter of the control circuit. Alternatively, the counter may log the number of detected high pressure conditions. Thus, initiating a delay based on a predetermined hold time and/or ceasing from further recovery attempts may be performed based on the count value or values of the counter. In order for the count value or values logged by the counter to be reset to zero, the control circuit may require certain conditions be met. One condition may be that the rotor speed return to the normal operating speed. In some examples, a second condition may be that no high pressure conditions are detected at the normal operating speed for a predetermined clearance time (e.g., 3 minutes).

The tasks described above and in FIGS. 7-9 and 12 are provided as examples. At least some of the tasks associated with FIGS. 7-9 and 12 may be performed in a different order than represented, performed concurrently or altogether omitted.

In the embodiment discussed above in connection with FIGS. 6-9, computation of flow rate is based on a particular function of BEMF, namely the rate of change or slope of the BEMF during open phase periods. However, other functions of BEMF may be used. For example, the function of BEMF may be simply the magnitude of BEMF detected. Stated another way, as used in this disclosure the expression "function of BEMF" includes BEMF itself as well as other functions of BEMF. Use of a function of BEMF as a parameter for flow rate determination is particularly advantageous because it is not necessary to incorporate any additional transducer into the pump. In effect, the coils of the pump act as the transducer to measure BEMF and thus measuring displacement of the rotor and, indirectly, measuring thrust on the rotor. However, other parameters related to thrust on the rotor may be employed instead of a function of BEMF. For example, where the pump is equipped with a transducer other than the coils which can directly measure the axial position of the rotor, control circuit 140 may determine the flow rate based in whole or in part on a signal from the transducer which represents displacement. Stated another way, the displacement is a parameter related to thrust on the rotor. Any other parameter related to thrust on the rotor can be used.

In the embodiments discussed above, the differential pressure determined by the control circuit is used to control the operation of the pump. In other embodiments, the control circuit may simply determine the differential pressure and/or flow rate and send a signal representing that data to an external device, and may not control operation of the pump.

The techniques described above may be used to determine the flow rate and/or differential pressure of pumped fluids other than blood. Moreover, although the above examples are focused on axial flow pumps, the techniques discussed above can be used with other pumps where the thrust on a rotor varies with flow rate as, for example, in certain radial-flow centrifugal pumps.

Additionally, in the embodiment discussed above in connection with FIGS. 11-13, it is not essential to compute either flow rate or differential pressure. The detection of a high pressure condition or clearance of a high pressure condition may be accomplished using the BEMF or a function of the BEMF directly. Typically, for a given rotor speed, a high pressure condition occurs at a corresponding threshold F(BEMF) value, and at a corresponding threshold flow rate value. Therefore, the control circuit may focus exclusively on the F(BEMF) values of FIG. 6 or the flow rate values of FIG. 10 while determining the presence of a high pressure condition. In other words, instead of correlating these values to a particular value of pressure, the detected F(BEMF) or flow values may be directly associated with the presence or absence of a high pressure condition.

As these and other variations and combinations of the features discussed above can be utilized without departing from the subject matter as defined by the claims, the foregoing description of exemplary aspects should be taken by way of illustration rather than by way of limitation of the subject matter as defined by the claims. It will also be understood that the provision of the examples described herein (as well as clauses phrased as "such as," "e.g.," "including" and the like) should not be interpreted as limiting the claimed subject matter to the specific examples; rather, the examples are intended to illustrate only some of many possible aspects.

The invention claimed is:

1. An implantable blood pump system comprising:
a pump including a housing having an axis, and a rotor disposed within the housing, the rotor being rotatable around the axis; and
a control circuit operatively coupled to the pump, the control circuit being configured to:
determine a flow rate of blood based at least in part on a parameter related to thrust on the rotor along the axis; and
determine a pressure condition of the pump based at least in part on the flow rate of blood, the pressure condition being a condition under which differential pressure across the pump equals or exceeds a threshold pressure value.

2. An implantable blood pump system as in claim 1, wherein the pump includes a stator operatively coupled to the control circuit, the stator incorporating a plurality of coils for applying a rotating magnetic field to the rotor.

3. An implantable blood pump system as in claim 2, wherein the parameter is based on back electromotive force (BEMF) in one or more of the plurality of coils.

4. An implantable blood pump system as in claim 1, wherein the control circuit includes a processor coupled to a memory, the memory storing a table that relates flow rates to corresponding amounts of differential pressure at the blood pump.

5. An implantable blood pump system as in claim 1 wherein the control circuit is operative to determine the differential pressure based on the flow rate and speed of rotation of the rotor.

6. A control circuit for monitoring the operation of an implantable blood pump, the control circuit comprising:
a flow rate determination circuit operative to determine a flow rate of blood based at least in part on a parameter related to thrust generated by a rotor of the pump; and
a pump pressure condition determination circuit operative to determine a pressure condition of the pump based at least in part on the determined flow rate of blood, the pressure condition being a condition under which differential pressure across the pump equals or exceeds a threshold pressure value.

7. A control circuit as in claim 6, wherein the pump pressure condition determination circuit is operative to determine the pressure condition of the pump based on the flow rate and speed of rotation of the rotor.

8. A control circuit as in claim 6, wherein the parameter is related to back electromotive force (BEMF) in a coil of the pump.

9. A control circuit as in claim 8, wherein: the control circuit is operable to sample voltage across a first coil of a stator of the pump during an open-phase period in which: (i) the first coil is not being driven, and (ii) at least one other coil in the stator is being driven; so as to evaluate a function of back electromotive force (BEMF) during the open-phase period, wherein the flow rate is determined based at least in part on the function of BEMF and speed of rotation of the rotor.

10. A control circuit as in claim 9, wherein the function of BEMF is a rate of change of the BEMF.

11. A control circuit as in claim 6, further comprising:
a processor; and
a memory coupled to the processor, the memory storing a table that relates different flow rates to different amounts of differential pressure at the blood pump for a given speed of rotation of the rotor.

12. A control circuit as in claim 6, further comprising a pump control module operative to control operation of the pump based at least in part on the determined pressure condition.

13. A method for monitoring operation of an implantable blood pump, the method comprising:
determining a flow rate of blood through the pump, wherein the flow rate is determined based at least in part on (i) a parameter relating to thrust generated by a rotor of the pump and (ii) speed of rotation of a rotor of the pump; and
determining a pressure condition of the pump based at least in part on the flow rate of blood, the pressure condition being a condition under which differential pressure across the pump equals or exceeds a threshold pressure value.

14. A method as in claim 13, further comprising:
sampling voltage across a first coil in the stator during an open-phase period in which: (i) the first coil is not being driven, and (ii) at least one other coil in the stator is being driven; and evaluating a function of back electromotive force (BEMF) during the open-phase period, wherein the flow rate is determined based on the function of BEMF and speed of rotation of the rotor; and
determining the speed of rotation of the rotor based on the sampled voltage.

15. A method as in claim 14, further comprising determining the flow rate of blood through the pump based at least in part on the magnitude of a current supplied to the pump.

16. A method as in claim 14, wherein the function of BEMF is a rate of change of BEMF.

17. A method as in claim 13, further comprising controlling the operation of the pump based on the determined pressure condition.

18. An implantable blood pump system comprising:
a pump including a housing having an axis, and a rotor disposed within the housing, the rotor being rotatable around the axis; and
a control circuit operatively coupled to the pump, the control circuit being configured to:
determine a differential pressure across the blood pump based at least in part on an initial speed of rotation of the rotor;
compare the differential pressure to a threshold pressure value;
determine the presence or absence of a high pressure condition based at least in part on the comparison; and
in response to determining the presence of a high pressure condition, determine an updated speed of rotation of the rotor, the updated speed being less than the initial speed.

19. An implantable blood pump system as in claim 18, wherein the control circuit is operative to determine differential pressure based further on a flow rate of blood.

20. An implantable blood pump system as in claim 18, the control circuit further including a pump control module operative to control operation of the pump based on the updated determined speed.

21. An implantable blood pump system as in claim 18, the control circuit further including a processor coupled to a memory, the memory storing one or more tables, the one or more tables relating flow rates to corresponding differential pressure values for a given speed of rotation of the rotor, wherein at least one table relates flow rates to differential pressure values at the initial speed.

22. An implantable blood pump system as in claim 18, wherein the control circuit is operative to determine the updated speed based on the speed of the rotor at which the presence of a high pressure condition is determined.

23. An implantable blood pump system as in claim 18, wherein the control circuit is further operative to:
determine differential pressure across the blood pump at the updated speed; and
delay determination of the differential pressure at the updated speed for a predetermined amount of time based on a count value indicative of a number of recovery attempts initiated.

24. A control circuit for monitoring the operation of an implantable blood pump, the control circuit comprising:
a differential pressure determination circuit operative to determine an amount of differential pressure across the blood pump;
a pressure condition determination circuit operative to determine whether the determined amount of differential pressure is at least equal to a differential threshold pressure value; and
an operating speed determination circuit operative to determine a reduced speed of rotation of the rotor based on the determination of the pressure condition determination circuit.

25. A control circuit as in claim 24, wherein the differential pressure determination circuit is operative to determine an amount of differential pressure based on a flow rate of blood.

26. A control circuit as in claim 24, further comprising:
a flow rate determination circuit operative to determine a flow rate of blood; and
a flow recovery determination circuit operative to determine whether the determined flow rate of blood is at least equal to a flow recovery threshold value,
wherein the operating speed determination circuit is further operative to determine an increased speed of rotation of the rotor if the determined flow rate of blood is at least equal to a flow recovery threshold value.

27. A control circuit as in claim 26, wherein the flow recovery threshold value is based on the speed of the rotor during determination of the flow rate of blood.

28. A method of monitoring operation of an implantable blood pump, comprising:
determining an amount of differential pressure across the pump at an initial speed of rotation of a rotor of the pump;
comparing the amount of differential pressure to a differential threshold pressure value determining the presence or absence of a high pressure condition at least partially based on the comparison; and in response to determining the presence of a high pressure condition, determining an updated speed of rotation of the rotor less than the initial speed.

29. A method as in claim 28, wherein determining an amount of differential pressure across the blood pump is based on a flow rate of blood.

30. A method as in claim 28, wherein determining an amount of differential pressure across the blood pump is based on a value of hematocrit for the patient.

31. A method as in claim 28, further comprising:
determining a flow rate of blood;
determining whether the determined flow rate of blood is at least equal to a flow recovery threshold value; and
if the determined flow rate of blood is at least equal to a flow recovery threshold value, increasing the speed of rotation of the rotor.

32. A method as in claim 31, wherein the flow recovery threshold value is based on the speed of the rotor during the determination of the flow rate of blood.

33. A method as in claim 28, wherein the updated speed of rotation of the rotor is determined based on a count value indicative of a number of recovery attempts initiated.

34. A method as in claim 28, wherein the method is repeatedly performed to regulate differential pressure across the pump.

35. A method as in claim 34, further comprising delaying performance of the method for a predetermined amount of time based on the determination of the presence of a high pressure condition and a count value indicative of a number of recovery attempts initiated.

36. A method as in claim 34, further comprising ceasing performance of the method based on the determination of the presence of a high pressure condition and a count value indicative of a number of retry cycles initiated.

* * * * *